United States Patent
Tsai et al.

[11] Patent Number: 6,135,987
[45] Date of Patent: Oct. 24, 2000

[54] SYNTHETIC FIBER

[75] Inventors: Fu-Jya Daniel Tsai; Brian Thomas Etzel, both of Appleton, Wis.

[73] Assignee: Kimberly-Clark Worldwide, Inc., Neenah, Wis.

[21] Appl. No.: 09/470,549

[22] Filed: Dec. 22, 1999

Related U.S. Application Data

[63] Continuation-in-part of application No. 08/995,981, Dec. 22, 1997.

[51] Int. Cl.$^7$ .......................... A61F 13/15; B32B 11/18; C08F 20/00

[52] U.S. Cl. .................. 604/365; 525/437; 525/444; 528/491; 428/113; 428/119; 428/137; 428/364; 264/165; 264/176.1; 264/211.12; 264/211.21; 264/211.22; 604/366; 604/367; 604/370; 604/372

[58] Field of Search .................... 525/437, 444; 528/491; 428/364, 113, 119, 137; 264/165, 176.1, 211.12, 211.21, 211.22; 604/365, 366, 367, 370, 372

[56] References Cited

U.S. PATENT DOCUMENTS

| | | | |
|---|---|---|---|
| 3,853,820 | 12/1974 | Vachon | 260/75 T |
| 3,921,333 | 11/1975 | Clendenning et al. | 47/37 |
| 3,964,486 | 6/1976 | Blaney | 128/284 |
| 4,137,921 | 2/1979 | Okuzumi et al. | 128/335.5 |
| 4,489,056 | 12/1984 | Himmelstein et al. | 424/22 |
| 4,685,909 | 8/1987 | Berg et al. | 604/360 |
| 4,710,187 | 12/1987 | Boland et al. | 604/385 A |
| 4,762,521 | 8/1988 | Roessler et al. | 604/38 SA |
| 4,770,656 | 9/1988 | Proxmire et al. | 604/393 |
| 4,789,592 | 12/1988 | Taniguchi et al. | 428/373 |
| 4,798,603 | 1/1989 | Meyer et al. | 604/378 |
| 4,931,488 | 6/1990 | Chiquet | 523/126 |
| 5,076,983 | 12/1991 | Loomis et al. | 264/101 |
| 5,216,050 | 6/1993 | Sinclair | 524/108 |
| 5,223,546 | 6/1993 | Morita et al. | 521/52 |
| 5,238,968 | 8/1993 | Morita et al. | 521/79 |
| 5,252,642 | 10/1993 | Sinclair et al. | 524/108 |
| 5,258,422 | 11/1993 | Chang et al. | 523/124 |
| 5,321,068 | 6/1994 | De Witt, Jr. | 524/321 |
| 5,336,552 | 8/1994 | Strack et al. | 428/224 |
| 5,340,646 | 8/1994 | Morita et al. | 428/307.3 |
| 5,424,346 | 6/1995 | Sinclair | 524/108 |
| 5,444,113 | 8/1995 | Sinclair et al. | 524/306 |
| 5,489,474 | 2/1996 | Shinoda et al. | 428/343 |
| 5,500,465 | 3/1996 | Krishnan et al. | 524/47 |
| 5,502,158 | 3/1996 | Sinclair et al. | 528/354 |
| 5,525,706 | 6/1996 | Gruber et al. | 528/354 |
| 5,545,681 | 8/1996 | Honkonen | 524/115 |
| 5,714,618 | 2/1998 | Kimura et al. | 549/263 |

FOREIGN PATENT DOCUMENTS

| | | |
|---|---|---|
| 0080274 | 6/1983 | European Pat. Off. . |
| 0394954 | 10/1990 | European Pat. Off. . |
| 0765913 | 4/1997 | European Pat. Off. . |
| 9204410 | 3/1992 | WIPO . |
| 9417226 | 8/1994 | WIPO . |
| 9508660 | 3/1995 | WIPO . |
| 9517216 | 6/1995 | WIPO . |

*Primary Examiner*—Samuel A. Acquah
*Attorney, Agent, or Firm*—Thomas J. Connelly; Douglas G. Glantz

[57] ABSTRACT

A process is disclosed for forming a synthetic fiber including providing a first component of an aliphatic polyester polymer a second component of a multicarboxylic acid, mixing the first component aliphatic polyester polymer and the second component multicarboxylic acid to form an unreacted specified thermoplastic composition, and melt blending the unreacted specified thermoplastic composition in an extruder or a mixer. The second component multicarboxylic acid lubricates the extruder and provides a nucleating agent for crystallizing the specified thermoplastic composition to form a mean crystal size less than about 120 Angstroms. Fiber composed of the specified thermoplastic composition has a mean crystal size less than about 120 Angstroms. The fiber has a glass transition temperature (Tg) less than about 55° C. In one aspect, a first component of polylactic acid and a second component of adipic acid provide synthetic fibers in a nonwoven structure used in a biodegradable and compostable disposable absorbent product for the absorption and removal of body fluids.

24 Claims, 2 Drawing Sheets

SYNTHETIC FIBER

This application is a CIP of Ser. No. 08/995,981 filed Dec. 22, 1997.

BACKGROUND OF THE INVENTION

1. Technical Field

This invention relates to a process for forming a synthetic fiber. In one aspect, this invention relates to a novel process for manufacturing a synthetic fiber composed of a specified thermoplastic composition.

2. Background

Disposable absorbent products currently find widespread use in many applications. In the infant care and child care markets, disposable diapers and training pants have replaced reusable cloth absorbent articles. Other widely successful disposable absorbent products include feminine care products such as sanitary napkins or tampons, adult incontinence products, and health care products such as surgical drapes or wound dressings.

A disposable absorbent product includes a composite structure including a topsheet, a backsheet, and an absorbent structure between the topsheet and backsheet. The disposable absorbent products include some type of fastening system for fitting the product onto the wearer.

Disposable absorbent products are subjected to one or more liquid insults, such as of water, urine, menses, or blood, during use. As such, the outer cover backsheet materials of the disposable absorbent products are made of liquid insoluble and liquid impermeable materials, such as polyolefin films, having sufficient strength and handling capability so that the disposable absorbent product retains its integrity during use by a wearer and does not allow leakage of the liquid insulting the product.

INTRODUCTION TO THE INVENTION

Although currently available disposable baby diapers and other disposable absorbent products have been accepted by the public, these current products still have need of improvement in specific areas. Many disposable absorbent products can be difficult to dispose. Attempts to flush many disposable absorbent products down a toilet into a sewage system may lead to blockage of the toilet or pipes connecting the toilet to the sewage system. The outer cover materials in the disposable absorbent products in particular do not disintegrate or disperse when flushed down a toilet so that the disposable absorbent product cannot be disposed in this way. If the outer cover materials are made very thin to reduce the overall bulk in an attempt to reduce the likelihood of blockage of a toilet or a sewage pipe, then the outer cover material does not exhibit sufficient strength to prevent tearing or ripping as the outer cover material is subjected to the stresses of normal use by a wearer.

Solid waste disposal is becoming an ever increasing problem throughout the world. As landfills continue to fill up, a demand has increased for a material source reduction in disposable products. As an alternative, recyclable or biodegradable components are needed to be developed for incorporating into the disposable products. As an alternative, products are needed to be developed for final disposal by means other than by incorporation into solid waste disposal facilities such as landfills.

Accordingly, there is a need for new materials to be used in disposable absorbent products which retain integrity and strength during use, but after such use, the materials may be disposed more efficiently. There is a need for new materials used in the disposable absorbent product to be disposed easily and efficiently by composting. Alternatively, the disposable absorbent product may be disposed easily and efficiently in a liquid sewage system wherein the disposable absorbent product is capable of being degraded.

Problems have been encountered with fibers prepared from aliphatic polyesters. Aliphatic polyester polymers have been observed to exhibit a relatively slow crystallization rate as compared to polyolefin polymers. The slow crystallization rate causes poor processability of the aliphatic polyester polymers.

The aliphatic polyester polymers do not provide sufficient thermal-dimensional stability. The aliphatic polyester polymers undergo severe heat shrinkage because of a relaxation of the polymer chain during downstream heat treatment processes, such as thermal bonding and lamination, unless an extra step such as heat setting is taken. However, a heat setting step limits the use of the fiber in in-situ nonwoven forming processes, such as spunbond and meltblown, where heat setting is very difficult. Moreover, the use of processing additives retards the biodegradation rate of the original material, or the processing additives themselves may not be biodegradable.

It is an object of the present invention to provide a novel process for forming a synthetic fiber.

It is another object of the present invention to provide a novel process for forming a synthetic fiber incorporating a specified thermoplastic composition.

It is an object of the present invention to provide a novel process for forming a synthetic fiber incorporating a thermoplastic composition providing preferred processability.

It is an object of the present invention to provide a novel process for forming a synthetic fiber incorporating a thermoplastic composition having a specified reduced crystal size.

It is an object of the present invention to provide a novel process for forming a synthetic fiber incorporating a thermoplastic composition having preferred thermal dimensional-stability.

It is an object of the present invention to provide a novel process for forming a synthetic fiber incorporating a thermoplastic composition having biodegradability.

It is an object of the present invention to provide an absorbent article formed by the novel process for forming a synthetic fiber incorporating a thermoplastic composition having preferred processability, thermal dimensional-stability, and biodegradability.

It is also an object of the present invention to provide a process for manufacturing a thermoplastic composition easily and efficiently formed into a fiber.

It is a further object of the present invention to provide a process for manufacturing a thermoplastic composition into a fiber for use in preparing nonwoven structures.

It is an object of the present invention to provide an absorbent article formed by the novel process for manufacturing a thermoplastic composition into a fiber for use in preparing nonwoven structures.

It is an object of the present invention to provide a fiber or nonwoven structure which is degradable in the environment.

These and other objects of the present invention will become more apparent from a careful inspection of the detailed description and the figure of the drawings which follow.

SUMMARY OF THE INVENTION

The present invention provides a process for forming a synthetic fiber including providing a first component of an aliphatic polyester polymer and a second component of a multi-carboxylic acid and melt blending the unreacted specified thermoplastic composition in an extruder. In one aspect, the present invention provides a process for forming a synthetic fiber including dry mixing the first component aliphatic polyester polymer and the second component multicarboxylic acid to form an unreacted specified thermoplastic composition. The second component multicarboxylic acid both lubricates the extruder and provides a nucleating agent for crystallizing the specified thermoplastic composition to form a mean crystal size less than about 120 Angstroms. Fiber composed of the specified thermoplastic composition has a mean crystal size less than about 120 Angstroms. The fiber has a glass transition temperature (Tg) lower than the Tg of the fiber without the multicarboxylic acid. In one aspect, the fiber has a glass transition temperature (Tg) less than about 55° C.

In one aspect, a first component of polylactic acid and a second component of adipic acid provide synthetic fibers in a nonwoven structure used in a biodegradable and compostable disposable absorbent product for the absorption and removal of body fluids.

DETAILED DESCRIPTION

Figure 1:
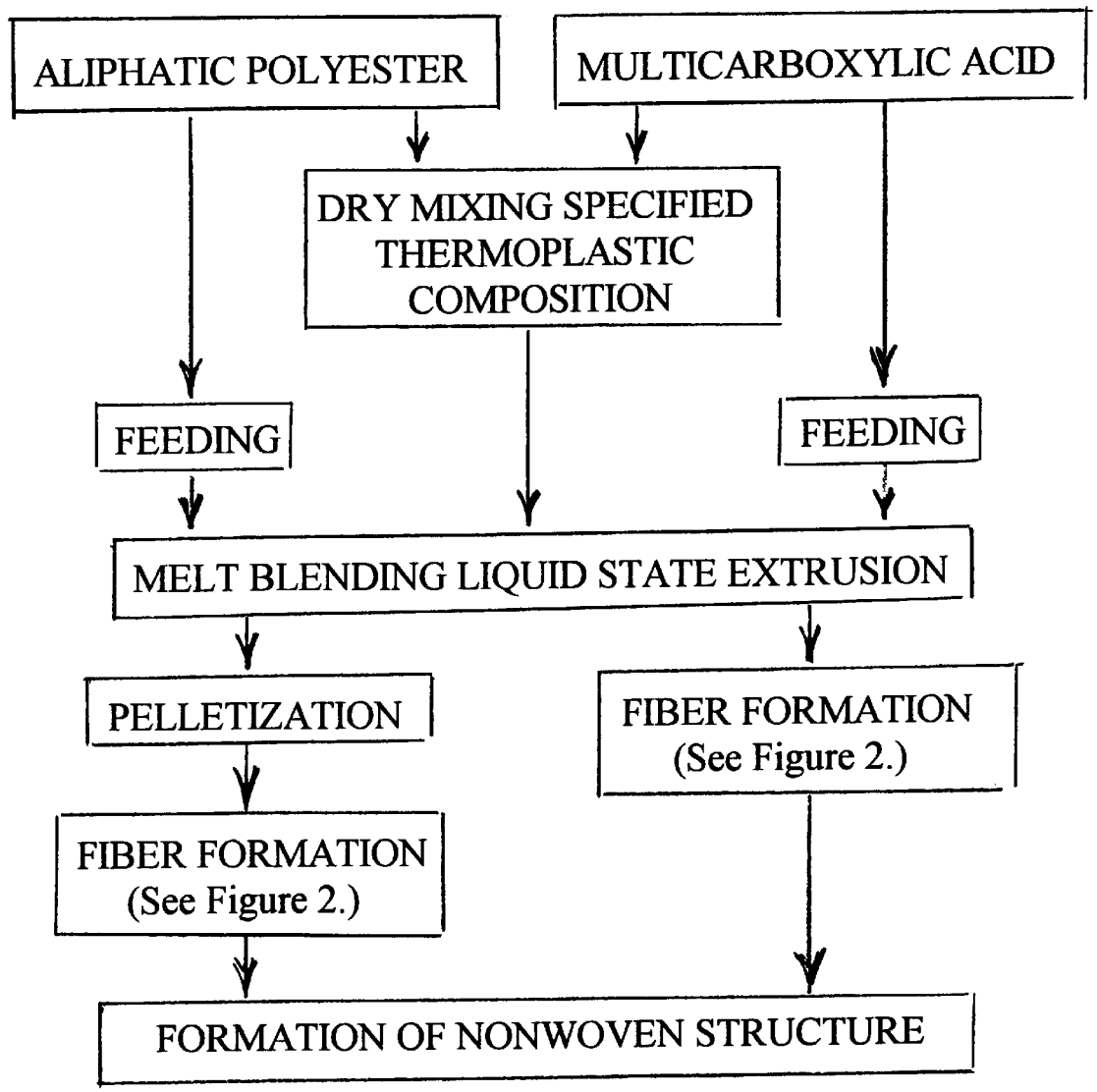
FIG. 1 shows a schematic block diagram of the process of the present invention.

The present invention provides a process for manufacturing a synthetic fiber. The process of the present invention provides a method for manufacturing a synthetic fiber composed of a specified thermoplastic composition.

In one aspect, the process of the present invention provides a method for manufacturing a synthetic fiber composed of a specified thermoplastic composition including an unreacted mixture of an aliphatic polyester polymer and a multicarboxylic acid.

In one aspect, the process of the present invention provides extruded fibers formed into nonwoven structures used in a disposable absorbent product intended for the absorption of fluids such as body fluids.

The process of the present invention incorporates a biodegradable thermoplastic composition which is easily prepared and readily processable into preferred final structures, such as fibers or nonwoven structures.

The process of the present invention incorporates a specified thermoplastic composition composed of a mixture of a first component and a second component. One embodiment of the specified thermoplastic composition includes a mixture of a first component of an aliphatic polyester polymer and a second component of a multicarboxylic acid, wherein the multicarboxylic acid has a total of carbon atoms less than about 30. It has been found that the specified thermoplastic composition as used in the process of the present invention provides preferred properties in a novel synthetic fiber formed by the process of the present invention.

In another aspect, the process of the present invention provides a nonwoven structure incorporating a synthetic fiber prepared from the specified thermoplastic composition. In one embodiment, such a nonwoven structure is used with a backsheet and an absorbent structure to provide a disposable absorbent product.

The process of the present invention produces a novel synthetic thermoplastic composition extruded into fibers. It has been found empirically that incorporating a specified weight percent of a multicarboxylic acid in the composition used in the process of the present invention provides for important advantages in extruding the fibers.

In extruding fibers in the process of the present invention, it has been found that the multicarboxylic acid beneficially exists in a liquid state during thermal processing of the thermoplastic composition but that during cooling of the processed thermoplastic composition, the multicarboxylic acid turns into a solid state, or crystallizes, at a higher temperature than before the aliphatic polyester polymer turns into a solid state, or crystallizes. In the specified thermoplastic composition used in the process of the present invention, the multicarboxylic acid performs two important and distinct functions.

First, when the thermoplastic composition is in a molten state, the multicarboxylic acid functions as a process lubricant or plasticizer, facilitating the processing of the thermoplastic composition while increasing the flexibility and toughness of a final product fiber through internal modification of the aliphatic polyester polymer. The multicarboxylic acid replaces the secondary valence bonds holding together the aliphatic polyester polymer chains with multicarboxylic acid-to-aliphatic polyester polymer valence bonds, facilitating the movement of the polymer chain segments. This effect is evidenced, in one embodiment of the present invention, in a poly(lactic acid) and adipic acid blend where the melting temperature of the thermoplastic composition shifts to lower temperatures with an increasing blend ratio of adipic acid to poly(lactic acid). With this effect, the torque needed to turn an extruder, in producing fibers, is reduced dramatically as compared with the processing of the poly(lactic acid) polymer alone. In addition, the process temperature required to spin the thermoplastic composition into a final product, such as a fiber or a nonwoven structure, is reduced dramatically, thereby decreasing the risk for undesirable thermal degradation of the poly(lactic acid) polymer.

Second, when a final product of the process of the present invention prepared from the thermoplastic composition of the present invention is being cooled and solidified from its liquid or molten state, the multicarboxylic acid functions as a nucleating agent. A nucleating agent, such as solid particulates, mixed with a thermoplastic composition provides sites for initiating crystallization during quenching. However, such solid nucleating agents agglomerate very easily in the thermoplastic composition resulting in the blocking of filters and spinneret holes during spinning. The nucleating effect of such solid nucleating agents peaks at add-on levels of about 1 percent of such solid nucleating agents. Both of these factors reduce the ability or the motivation to add in high weight percentages of such solid nucleating agents into the thermoplastic composition.

In the processing of the specified thermoplastic composition of the present invention, however, it has been found empirically that the multicarboxylic acid exists in a liquid state during the extrusion process, wherein the multicarboxylic acid functions as a plasticizer, while the multicarboxylic acid is still able to solidify or crystallize before the aliphatic polyester during cooling, wherein the multicarboxylic acid functions as a nucleating agent. Upon cooling from the homogeneous melt, the multicarboxylic acid solidifies or crystallizes relatively more quickly and completely just as it falls below its melting point since it is a relatively small molecule. For example, adipic acid has a melting temperature of about 162° C. and a crystallization temperature of about 145° C.

Figure 2:
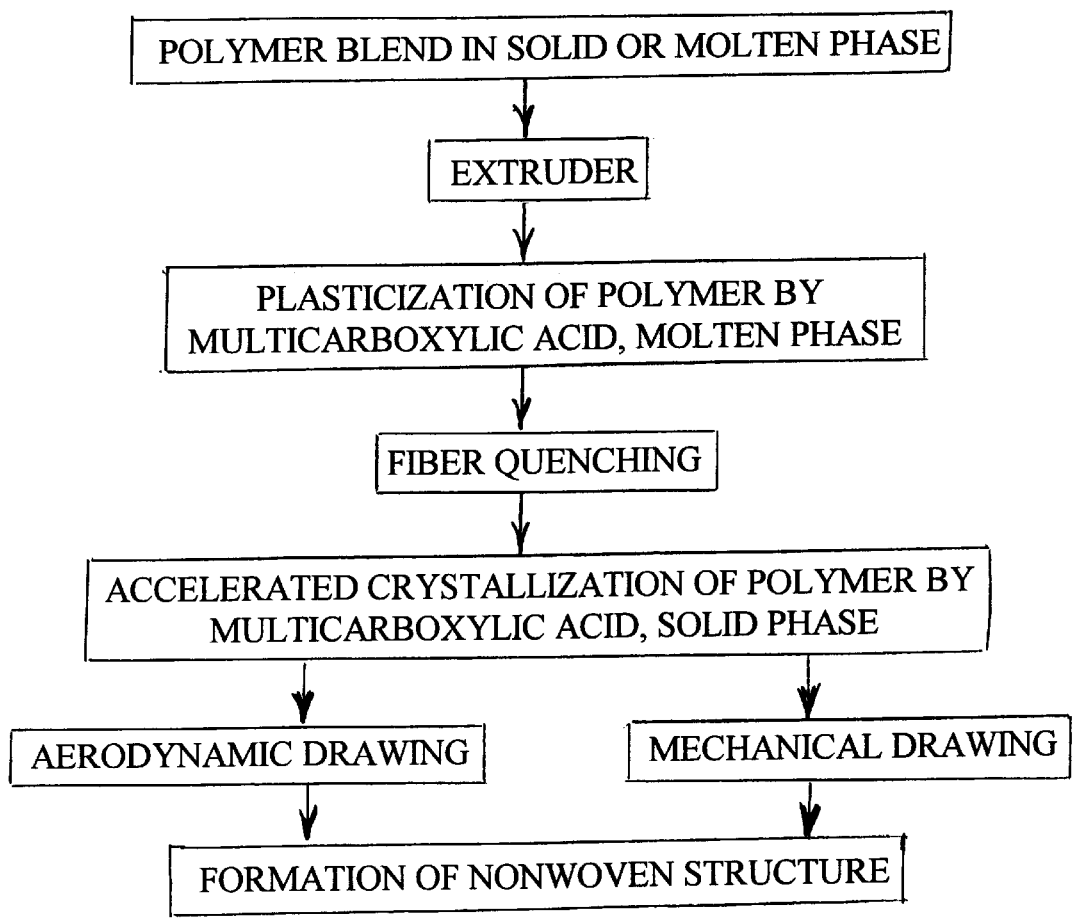
FIG. 2 shows a schematic block diagram of the process of the present invention, highlighting the fiber formation.

Referring now to FIG. 1 and FIG. 2, block schematic diagrams show a process flow depiction for the process of the present invention.

In FIG. 1, the first component composed of the aliphatic polyester is shown as it is combined with the second component composed of the multicarboxylic acid through two different modes. The first mode adds the first component aliphatic polyester and second component multicarboxylic acid separately into either a melt blender or melt extruder. The second mode dry mixes the first component aliphatic polyester and second component multicarboxylic acid together before adding that resultant dry mixture to a melt blender or melt extruder. From the molten state extrusion which takes place in both the melt blender or melt extruder, there are two paths to the formation of a nonwoven structure. The first path has the molten extrudate being cooled and pelletized or formed into a form functional for being fed into an extrusion device for the purpose of fiber formation. The second path directly goes to the fiber formation of a nonwoven structure from the molten extrudate. The fiber formation step is further expanded upon in the FIG. 2 block schematic.

The FIG. 2 schematic highlights the dual functionality of the second component multicarboxylic acid during the molten and fiber forming phases as the first component and second component are processed together. When the first component aliphatic polyester and second component multicarboxylic acid are combined and existing in a molten phase, the first component aliphatic polyester is plasticized by the multicarboxylic acid. When the molten blend is formed into fibers, the molten blend cools and the second component multicarboxylic acid solidifies and accelerates the crystallization of the first component aliphatic polyester. This acceleration of crystallization is manifested by an increase in crystal density and a decrease in crystal size. Typically, following fiber formation, the fibers are aerodynamically or mechanically drawn, which further quenches and crystallizes the fibers as they are formed into a nonwoven structure.

The process of the present invention produces a novel synthetic fiber. In one aspect, the process of the present invention provides a novel synthetic fiber having a mean crystal size less than 120 Angstroms.

It has been found empirically that the novel synthetic fiber product manufactured by the specified process of the present invention exhibits a crystal size effective for the fiber product made from the specified thermoplastic composition to provide preferred properties, when thermally processed, as a fiber having a mean crystal size less than 120 Angstroms.

The aliphatic polyester macromolecule polymer alone, when taken separately and apart from the specified composition used in the process of the present invention has a slow crystallization rate. When cooled, the aliphatic polyester macromolecule polymer alone solidifies or crystallizes more slowly and to a larger crystal size and at a temperature lower than its melting temperature. For example, poly(lactic acid) alone, when taken separately and apart from the specified composition used in the process of the present invention has a melting temperature of about 175° C. and a crystallization temperature of about 121° C. In the formation of the fiber product manufactured by the process of the present invention during cooling, the multicarboxylic acid used in the process of the present invention initiates crystallization at a temperature higher than the natural crystallization temperature of the aliphatic polyester polymer and acts as solid nucleating sites within the cooling thermoplastic composition.

The fiber made from the specified composition used in the process of the present invention has been found to exhibit a crystal size that is effective for the fiber made from the specified composition of the present invention to provide preferred properties. The fiber made from the specified composition of the present invention has been found to exhibit a Mean Crystal Size less than about 120 Angstroms. The Mean Crystal Size of a material is determined according to the procedure described in the Test Methods section.

The novel synthetic fiber of the present invention having a Mean Crystal Size less than about 120 Angstroms has been found to eliminate the heat shrinkage problem encountered with fibers prepared from only aliphatic polyester polymers. The novel fiber having a Mean Crystal Size less than about 120 Angstroms has been found to eliminate the heat-shrinkage from thermally-induced chain relaxation of the polymer segments in the amorphous phase and incomplete crystalline phase. The novel synthetic fiber maximizes the crystallization of the material before the bonding stage so that the thermal bonding energy goes directly to melting rather than to allow for chain relaxation and reordering of the incomplete crystalline structure. The fiber of the present invention empirically has been found to maximize the crystallization of the aliphatic polyester polymer and minimize heat shrinkage.

The process of the present invention incorporates a specified thermoplastic composition which includes a first component and a second component. As used herein, by the term "thermoplastic" is meant a material that softens when exposed to heat and substantially returns to its original condition when cooled to room temperature.

The first component in the specified thermoplastic composition is an aliphatic polyester polymer. Suitable aliphatic polyester polymers include, but are not limited to, poly (lactic acid), polybutylene succinate, polybutylene succinate-co-adipate, polyhydroxybutyrate-valerate, polyhydroxybutyrate-covalerate, polycaprolactone, copolyester, polyester amide, starch-based polymers, mixtures of such polymers, or copolymers of such polymers. Other potentially suitable polymers include polyethylene terephthalate-based polymer, sulfonated polyethylene terephthalate, polyethylene oxide, polyethylene, polypropylene, polyvinyl alcohol, and aliphatic aromatic copolyester.

The process of the present invention incorporates a novel composition composed of an aliphatic polyester polymer and a multicarboxylic acid in a specified amount of 5–50 weight percent, preferably providing the multicarboxylic acid in an amount of 10–40 weight percent, more preferably 20–40 weight percent, most preferably 25–30 weight percent. The aliphatic polyester polymer is incorporated in the specified thermoplastic composition in a weight amount between about 50 weight percent to about 95 weight percent. Below about 5% by weight, unacceptable shrinkage occurs. Above about 50% by weight, the fibers become unacceptably weak.

In a preferred embodiment, aliphatic polyester polymer is incorporated in the thermoplastic composition in a weight amount between about 70 weight percent to about 75 weight percent.

In a preferred embodiment, multicarboxylic acid is incorporated in the thermoplastic composition in a weight amount between about 25 weight percent to about 30 weight percent.

In a preferred embodiment, the process of the present invention forms a novel synthetic fiber having a mean crystal size less than 120 Angstroms.

In one embodiment of the process of the present invention, it is preferred that the aliphatic polyester polymer used is poly(lactic acid). Poly(lactic acid) polymer is prepared by the polymerization of lactic acid. A chemically equivalent material may be prepared by the polymerization of lactide. As such, as used herein, the term "poly(lactic acid) polymer" is intended to represent the polymer prepared by either the polymerization of lactic acid or lactide.

Lactic acid and lactide are asymmetrical molecules having two optical isomers referenced to as the levorotatory enantiomer and the dextrorotatory enantiomer, respectively. Levorotatory enantiomer is sometimes referred to as "L," and dextrorotatory enantiomer is sometimes referred to as "D." Different polymers, which are chemically similar yet which have different properties, can be prepared by polymerizing a particular enantiomer or by using a mixture of the two enantiomers. It has been found that by modifying the stereochemistry of a poly(lactic acid) polymer, we can control the melting temperature, melt rheology, and crystallinity of the polymer. By controlling such properties, we can prepare a multicomponent fiber having preferred melt strength, mechanical properties, softness, and processability properties to make attenuated, heat set, and crimped fibers.

The aliphatic polyester polymer should be present in the specified thermoplastic composition in an amount effective to result in the thermoplastic composition having preferred properties. The aliphatic polyester polymer should be present in the thermoplastic composition in a weight amount that is less than 100 weight percent, in the range of between about 40 weight percent to less than 100 weight percent, preferably between about 50 weight percent to about 95 weight percent, more preferably between about 60 weight percent to about 90 weight percent, even more preferably between about 60 weight percent to about 80 weight percent, and most preferably between about 70 weight percent to about 75 weight percent, wherein all weight percents are based on the total weight amount of the aliphatic polyester polymer and the multicarboxylic acid present in the specified thermoplastic composition.

The aliphatic polyester polymer should have a weight average molecular weight effective for the specified thermoplastic composition to provide preferred melt strength, fiber mechanical strength, and fiber spinning properties. If the weight average molecular weight of an aliphatic polyester polymer is too high, the polymer chains are heavily entangled which may result in a thermoplastic composition incorporating that aliphatic polyester polymer being difficult to process. Conversely, if the weight average molecular weight of an aliphatic polyester polymer is too low, the polymer chains are not entangled enough, and the thermoplastic composition incorporating that aliphatic polyester polymer has a relatively weak melt strength, making high speed processing very difficult.

The aliphatic polyester polymers used in the process of the present invention have weight average molecular weights between about 10,000 to about 2,000,000, preferably between about 50,000 to about 400,000, and more preferably between about 100,000 to about 300,000.

The Weight Average Molecular Weight for polymers or polymer blends is determined using a method as described in the Test Methods section herein.

The aliphatic polyester polymer should have a polydispersity index value effective for the specified thermoplastic composition to provide preferred melt strength, fiber mechanical strength, and fiber spinning properties. As used herein, by "polydispersity index" is meant the value obtained by dividing the weight average molecular weight of a polymer by the number average molecular weight of the polymer. If the polydispersity index value of an aliphatic polyester polymer is too high, a thermoplastic composition incorporating that aliphatic polyester polymer is difficult to process because of inconsistent processing properties caused by polymer segments including low molecular weight polymers having lower melt strength properties during spinning. The aliphatic polyester polymer should have a polydispersity index value between about 1 to about 15, preferably between about 1 to about 4, and most preferably between about 1 to about 3.

The Number Average Molecular Weight for polymers or polymer blends is determined using a method as described in the Test Methods section herein.

The aliphatic polyester polymer should be melt processable. The aliphatic polyester polymer should have a melt flow rate between about 1 gram per 10 minutes to about 200 grams per 10 minutes, preferably between about 10 grams per 10 minutes to about 100 grams per 10 minutes, and more preferably between about 20 grams per 10 minutes to about 40 grams per 10 minutes. The melt flow rate of a material is determined according to ASTM Test Method D1238-E incorporated in its entirety herein by reference.

In a preferred embodiment of the process of the present invention, the aliphatic polyester polymer is biodegradable. The specified thermoplastic composition incorporating the aliphatic polyester polymer, in the form of a fiber or in the form of a nonwoven structure, will be biodegradable when disposed to the environment and exposed to air (oxygen) and/or water.

As used herein, by "biodegradable" is meant that a material degrades from the action of naturally occurring microorganisms such as bacteria, fungi, and algae.

In the process of the present invention, the aliphatic polyester polymer should be compostable. The specified thermoplastic composition incorporating the aliphatic polyester polymer, either in the form of a fiber or in the form of a nonwoven structure, is compostable when disposed to the environment and exposed to air or water or a combination of air and water.

As used herein, by the term "compostable" is meant a material capable of undergoing biological decomposition in a compost site such that the material is not visually distinguishable and breaks down into carbon dioxide, water, inorganic compounds, and biomass at a rate consistent with known compostable materials.

The second component in the thermoplastic composition is a multicarboxylic acid. A multicarboxylic acid is an acid incorporating two or more carboxylic acid groups. The process of the present invention uses dicarboxylic acids, which provide two carboxylic acid groups. The multicarboxylic acid should have a total number of carbons not so large that crystallization kinetics will be slowed. The crystallization kinetics determines the speed at which crystallization occurs. The multicarboxylic acid should have a total of carbon atoms less than about 30, preferably between about 3 to about 30, more preferably between about 4 to about 20, and most preferably between about 5 to about 10. Examples of the multicarboxylic acids of present invention are malonic acid, citric acid, succinic acid, glutaric acid, adipic acid, pimelic acid, suberic acid, azelaic acid, roccellic acid, itaconic acid, fumaric acid, phthalic acid, terephthalic acid, or sebacic acid, and mixtures thereof.

The multicarboxylic acid should be present in the specified thermoplastic composition in an amount effective to result in the thermoplastic composition having preferred properties. The multicarboxylic acid is present in the specified thermoplastic composition in a weight amount greater than 0 weight percent up to about 60 weight percent, preferably between about 5 weight percent to about 50 weight percent, more preferably between about 10 weight percent to about 40 weight percent, even more preferably between about 20 weight percent to about 40 weight percent, and most preferably between about 25 weight percent to about 30 weight percent. All weight percents are based on the total weight amount of the aliphatic polyester polymer and the multicarboxylic acid present in the specified thermoplastic composition.

For the specified thermoplastic composition of the present invention to be processed into a product such as a fiber or a nonwoven structure having the preferred properties, it has been discovered that the multicarboxylic acid should exist in a liquid state or a molten state during thermal processing of the specified thermoplastic composition. The novel process is applied to any polymers that the multicarboxylic acid can serve the dual functions of the multicarboxylic acid in the process of the present invention.

It has been discovered further that during cooling of the processed specified thermoplastic composition, the multicarboxylic acid transforms into a solid state, or crystallizes, before the aliphatic polyester polymer turns into a solid state, or crystallizes.

In the thermoplastic composition of the process of the present invention, the multicarboxylic acid performs two important, but distinct, functions.

The first important, but distinct, function is found when the thermoplastic composition is in a liquid or molten state, the multicarboxylic acid functions as a process lubricant or plasticizer which facilitates the processing of the thermoplastic composition while increasing the flexibility and toughness of a final product, i.e., a fiber or a nonwoven structure, through internal modification of the aliphatic polyester polymer. The multicarboxylic acid replaces the secondary valence bonds holding together the aliphatic polyester polymer chains with multicarboxylic acid-to-aliphatic polyester polymer valence bonds, thereby facilitating the movement of the polymer chain segments. The replacement effect has been found in a poly(lactic acid) and adipic acid blend where the melting temperature of the specified thermoplastic composition shifted to lower temperatures with an increasing blend ratio of adipic acid to poly(lactic acid). With this effect, the torque needed to turn an extruder is reduced dramatically compared with the processing of the poly(lactic acid) polymer alone.

The process temperature required to spin the thermoplastic composition into a final product, such as a fiber or a nonwoven structure, is reduced dramatically, thereby decreasing the risk for undesirable thermal degradation of the aliphatic polyester polymers.

The second important, but distinct function is found when a final product prepared from the specified thermoplastic composition, such as a fiber or a nonwoven structure, is being cooled and solidified from its liquid or molten state, the multicarboxylic acid functions as a nucleating agent. Aliphatic polyester polymers have a very slow crystallization rate. Two ways resolve this issue. One way changes the cooling temperature profile to maximize the crystallization kinetics. The other way adds a nucleating agent to increase the sites and degree of crystallization.

The process of cooling the extruded polymer to ambient temperature is achieved by blowing ambient or sub-ambient temperature air over the extruded polymer. The quenching or super-cooling changes the temperature greater than 100° C. and most often greater than 150° C. over a relatively short time frame (seconds). To customize the process further into the ideal cooling temperature profile needed to be the sole method of maximizing the crystallization kinetics of aliphatic polyesters in a real manufacturing process is very difficult because of the extreme cooling needed within a very short period of time. Cooling can be used in combination with a second method of modification, though. The second method is to have a nucleating agent, such as solid particulates, mixed with a thermoplastic composition to provide sites for initiating crystallization during quenching. However, such solid nucleating agents agglomerate very easily in the thermoplastic composition which can result in the blocking of filters and spinneret holes during spinning. The nucleating effect of such solid nucleating agents peaks at add-on levels of about 1 percent of such solid nucleating agents. Both of these factors reduce the ability to add high weight percentages of solid nucleating agents into the thermoplastic composition.

In the processing of the specified thermoplastic composition of the present invention, it has been found that the multicarboxylic acid exists in a liquid (molten) state during the extrusion process, wherein the multicarboxylic acid functions as a plasticizer, while the multicarboxylic acid is still able to solidify or crystallize before the aliphatic polyester during cooling, wherein the multicarboxylic acid functions as a nucleating agent. Upon cooling from the homogeneous melt, the multicarboxylic acid solidifies or crystallizes relatively more quickly and completely just as it falls below its melting point since it is a relatively small molecule. In one embodiment, adipic acid has a melting temperature of about 162° C. and a crystallization temperature of about 145° C.

The aliphatic polyester polymer, being a macromolecule, has a relatively very slow crystallization rate. When cooled, it solidifies or crystallizes more slowly and at a temperature lower than its melting temperature. In one embodiment, poly(lactic acid) has a melting temperature of about 175° C. and a crystallization temperature of about 121° C. During such cooling, the multicarboxylic acid starts to crystallize before the aliphatic polyester polymer and acts as solid nucleating sites within the cooling thermoplastic composition.

A thermally processed thermoplastic composition or a product made from such a thermoplastic composition, such as a fiber or a nonwoven structure, exhibits a crystal size effective for the specified thermoplastic composition or a product made from the thermoplastic composition to exhibit preferred properties. In one embodiment of the process of the present invention, a thermally processed thermoplastic composition or a product made from such a thermoplastic composition, such as a fiber or a nonwoven structure, exhibits a Mean Crystal Size less than about 120 Angstroms, preferably less than about 110 Angstroms, more preferably less than about 100 Angstroms, even more preferably less than about 80 Angstroms, and most preferably less than about 70 Angstroms. The Mean Crystal Size of a material is determined according to the procedure described in the Test Methods section herein.

While the principal components of the specified thermoplastic composition of the process of the present invention have been described in the foregoing, such thermoplastic composition is not limited to components consisting of the principal components. The specified thermoplastic composition can include other components not adversely affecting the preferred properties of the thermoplastic composition. Exemplary materials used as additional components include pigments, antioxidants, stabilizers, surfactants, waxes, flow promoters, solid solvents, plasticizers, nucleating agents, particulates, and materials added to enhance processability of the thermoplastic composition. An example of such an optional component is a surface modified particulate available, for example, from Burgess Pigment Company of Sandersville, Ga. under the designation Burgess Polyclay surface modified particulate, or from Barretts Minerals Inc. of Dillon, Mont. under the designation Micropflex 1200 surface modified particulate. If such additional components are included in a specified thermoplastic composition, the additional components should be used in an amount less than about 5 weight percent, preferably less than about 3 weight percent, and more preferably less than about 1 weight percent, wherein all weight percents are based on the total weight amount of the aliphatic polyester polymer, the multicarboxylic acid, and the additional components present in the specified thermoplastic composition.

The specified thermoplastic composition of the process of the present invention is a mixture of the aliphatic polyester polymer, the multicarboxylic acid, and, optional additional components.

To achieve the preferred properties for the specified thermoplastic composition of the process of the present invention, it has been discovered that it is critical that the aliphatic polyester polymer and the multicarboxylic acid remain substantially unreacted with each other such that a copolymer incorporating each of the aliphatic polyester polymer and the multicarboxylic acid is not formed. As such, each of the aliphatic polyester polymer and the multicarboxylic acid remains distinct components of the specified thermoplastic composition.

In one embodiment of the process of the present invention, after dry mixing together the aliphatic polyester polymer and the multicarboxylic acid to form a specified thermoplastic composition dry mixture, such thermoplastic composition dry mixture is preferably agitated, stirred, or otherwise blended effectively to mix uniformly the aliphatic polyester polymer and the multicarboxylic acid such that an essentially homogeneous dry mixture is formed. The dry mixture then is melt blended in an extruder effectively to mix the aliphatic polyester polymer and the multicarboxylic acid uniformly such that a substantially homogeneous melted mixture is formed. The homogeneous melted mixture then is cooled and pelletized. Alternatively, the homogeneous melted mixture is sent directly to a spin pack or other equipment for forming fibers or for forming a nonwoven structure. Alternative methods of mixing together the components used in the process of the present invention include adding the multicarboxylic acid to the aliphatic polyester in an extruder used to mix the components together. An initial melt mix of both of the components can bring together the components at the same time.

To determine if the aliphatic polyester polymer and the multicarboxylic acid remain essentially unreacted, techniques of nuclear magnetic resonance and infrared analysis can evaluate the chemical characteristics of the final thermoplastic composition.

The melting or softening temperature of the thermoplastic composition should be within a range between about 25° C. to about 350° C., preferably between about 55° C. to about 300° C., and more preferably between about 100° C. to about 200° C.

The thermoplastic composition of the present invention has been found to exhibit preferred processability properties as compared to a thermoplastic composition incorporating the aliphatic polyester polymer but none of the multicarboxylic acid. As used herein, the preferred method to determine the improved processability of a thermoplastic composition is by measuring a decline in the glass transition temperature (Tg). At the glass transition temperature, the polymer chains in the thermoplastic composition begin segmental motion which means that there is enough energy, usually thermal energy, to allow the bulk polymer to flow. A decline in the glass transition temperature means that it takes less thermal energy to induce this segmental motion and the resultant flow. A thermoplastic composition processed at a relatively lower temperature has components of the thermoplastic composition less vulnerable to thermal degradation. A thermoplastic composition having a lowered glass transition temperature is processed in equipment such as an extruder operated at lower power settings such as using less torque to turn the screw of the extruder.

The specified thermoplastic composition has a lowered glass transition temperature and requires less energy to process and is more economical to use in forming fibers.

In one embodiment of the process of the present invention, the specified thermoplastic composition or a product made from such a specified thermoplastic composition, such as a fiber or nonwoven structure, has a glass transition temperature (Tg) less than about 55° C., preferably less than about 50° C., more preferably less than about 45° C., and most preferably less than about 40° C.

The selection of the starting polymer affects the glass transition temperature (Tg). Different aliphatic polyesters have different glass transition temperatures (Tg) depending on chemical composition of the polymer molecule, the weight average molecular weight, the number average molecular weight, the polydispersity index, the amount of residual monomer, and the amount of other impurities.

The selection of the multicarboxylic acid affects the amount of suppression of the glass transition temperature, (delta Tg), of the thermoplastic composition compared with the glass transition temperature of the starting polymer.

In one embodiment of the composition and process of the present invention, the specified thermoplastic composition or the product made from the specified thermoplastic composition, such as a fiber or nonwoven structure, has a suppression in glass transition temperature, (delta Tg), of at least 3 degrees centigrade, preferably at least 5 degrees centigrade, more preferably at least about 10 degrees centigrade, and in some cases, greater than 20 degrees centigrade.

As used herein, by the term "fiber" or "fibrous" is meant a material wherein the length to diameter ratio of such material is greater than about 10. Conversely, by the term "nonfiber" or "nonfibrous" material is meant a material wherein the length to diameter ratio of such material is about 10 or less.

The melt spinning of polymers includes the production of continuous filament, such as spunbond or meltblown, and non-continuous filament, such as staple and short-cut fibers, structures. To form a spunbond or meltblown fiber, a thermoplastic composition is extruded and fed to a distribution system where the thermoplastic composition is introduced into a spinneret plate. The spun fiber then is cooled, solidified, drawn by an aerodynamic system, and then is formed into a conventional nonwoven. To produce short-cut or staple, the spun fiber is cooled, solidified, and drawn by a mechanical rolls system to an intermediate filament diameter and collected fiber, rather than being directly formed into a nonwoven structure. Subsequently, the collected fiber is "cold drawn" at a temperature below its softening temperature to the preferred finished fiber diameter, which process step can be followed by crimping/texturizing and cutting to a desirable fiber length.

Fibers can be cut into relatively short lengths, such as staple fibers which have lengths in the range of about 25 to about 50 millimeters and short-cut fibers which are even shorter and have lengths less than about 18 millimeters. See, for example, U.S. Pat. No. 4,789,592 to Taniguchi et al. and U.S. Pat. No. 5,336,552 to Strack et al., both of which are incorporated herein by reference in their entirety.

One problem encountered with preparing fibers from only aliphatic polyester polymers is that such fibers experience heat shrinkage during downstream thermal processing. The heat-shrinkage mainly occurs because of the thermally-induced chain relaxation of the polymer segments in the amorphous phase and incomplete crystalline phase. To overcome this problem, the crystallization of the material should be maximized before the bonding stage so that the thermal energy goes directly to melting rather than to allow for chain relaxation and reordering of the incomplete crystalline structure. The material can be subjected to a heat-setting treatment. When the fibers subjected to heat-setting reach the bonding roll, the fibers will not shrink substantially because such fibers are already fully or highly oriented. However, in spunbond and meltblown processes, an in-line heat-setting process is very difficult.

The process of the present invention alleviates the need for, but does not prohibit, a heat-setting step because the use of the multicarboxylic acid in the specified thermoplastic composition allows for the usage of existing spunbond and melt-blown assets without major process modification. The blending of the aliphatic polyester polymer with a multicarboxylic acid maximizes both the crystallization rate and total crystalinity of the aliphatic polyester polymer which minimizes the expected heat shrinkage of the aliphatic polyester polymer.

When preparing a short-cut or staple fiber including in-line heat setting, in one embodiment of the process of the present invention, the fibers prepared from the thermoplastic composition of the process of the present invention undergo heat setting. Heat setting further reduces heat shrinkage of the fiber. The heat-setting can be done when the fibers are subjected to a constant strain, which can be, but is not limited to, about 10 to about 20 percent, at a temperature greater than about 50° C., preferably greater than about 70° C., and more preferably greater than about 90° C. The highest heat-setting conditions are preferred, including both applied strain and temperatures, while not sacrificing a fiber's processability. However, too high of a heat setting temperature such as, for example, a temperature close to the melting temperature of a component of a fiber, reduces the fiber strength and results in the fiber being hard to handle because of tackiness.

In one embodiment of the process of the present invention, a fiber prepared from the specified thermoplastic composition of the process of the present invention has a shrinking amount at a temperature of about 100° C. and for a time period of about 15 minutes quantified as a Heat Shrinkage value less than about 15 percent, preferably less than about 10 percent, more preferably less than about 5 percent, and most preferably less than about 2 percent, wherein the amount of shrinking is based on the difference between the initial and final lengths of the fiber divided by the initial length of the fiber multiplied by 100. The Heat Shrinkage value for a fiber may be determined according to the procedure described in the Test Methods section herein.

The specified thermoplastic composition of the process of the present invention is suited particularly for preparing fibers or nonwoven structures used in disposable products including disposable absorbent products such as diapers, adult incontinent products, and bed pads; in catamenial devices such as sanitary napkins and tampons; and other absorbent products such as wipes, bibs, wound dressings, and surgical capes or drapes. Accordingly, in one aspect, the process of the present invention provides a disposable absorbent product incorporating the multicomponent fibers produced by the process of the present invention.

In one embodiment of the process of the present invention, the specified thermoplastic composition is formed into a fibrous matrix for incorporation into a disposable absorbent product. A fibrous matrix may take the form of a fibrous nonwoven web. Fibrous nonwoven webs may be made completely from fibers prepared from the specified thermoplastic composition used in the process of the present invention or they may be blended with other fibers. The length of the fibers used may depend on the particular end use contemplated. Where the fibers are to be degraded in water as, for example, in a toilet, the lengths are maintained at or below about 15 millimeters.

In one embodiment of the process of the present invention, a disposable absorbent product is provided, which disposable absorbent product includes a liquid-permeable topsheet, a backsheet attached to the liquid-permeable topsheet, and an absorbent structure positioned between the liquid-permeable topsheet and the backsheet, wherein both the topsheet and backsheet include fibers prepared from the specified thermoplastic composition of the process of the present invention.

Exemplary disposable absorbent products are described in U.S. Pat. No. 4,710,187; U.S. Pat. No. 4,762,521; U.S. Pat. No. 4,770,656; and U.S. Pat. No. 4,798,603; which references are incorporated herein by reference.

Absorbent products and structures according to all aspects of the process of the present invention are subjected to multiple insults of a body liquid during use. Accordingly, the absorbent products and structures should be capable of absorbing multiple insults of body liquids in quantities to which the absorbent products and structures will be exposed during use. The insults are separated from one another by a period of time.

Test Methods

Melting Temperature

The melting temperature of a material was determined using differential scanning calorimetry. A differential scanning calorimeter, available from T. A. Instruments Inc. of New Castle, Del., under the designation Thermal Analyst 2910 Differential Scanning Calorimeter (DSC), which was outfitted with a liquid nitrogen cooling accessory and used in combination with Thermal Analyst 2200 analysis software program, was used for the determination of melting temperatures.

The material samples tested were either in the form of fibers or resin pellets. It is preferred not to handle the material samples directly, but rather to use tweezers and other tools, so as not to introduce anything that would produce erroneous results. The material samples were cut in the case of fibers, or placed in the case of resin pellets, into an aluminum pan and weighed to an accuracy of 0.01 mg on an analytical balance. If needed, a lid was crimped over the material sample onto the pan. The differential scanning calorimeter was calibrated using an indium metal standard, and a baseline correction was performed as described in the manual for the differential scanning calorimeter. A material sample was placed into the test chamber of the differential scanning calorimeter for testing and an empty pan is used as a reference. All testing was run with a 55 cubic centimeter/minute nitrogen (industrial grade) purge on the test chamber. The heating and cooling program is a 2 cycle test that begins with equilibration of the chamber to −75° C., followed by a heating cycle of 20° C./minute to 220° C., followed by a cooling cycle at 20° C./minute to −75° C., and then another heating cycle of 20° C./minute to 220° C. The results were evaluated using the analysis software program wherein the glass transition temperature (Tg) of inflection, endothermic, and exothermic peaks were identified and quantified. The glass transition temperature was identified as the area on the line where a distinct change in slope occurs, and then the melting temperature was determined using an automatic inflection calculation.

Apparent Viscosity

A capillary rheometer, available from Gottfert of Rock Hill, S.C., under the designation Gottert Rheograph 2003 capillary rheometer was used in combination with Win-RHEO (version 2.31) analysis software to evaluate the apparent viscosity rheological properties of material samples. The capillary rheometer setup included a 2000 bar pressure transducer and a 30/1:0/180 round hole capillary die.

If the material sample being tested demonstrated or was known to have water sensitivity, the material sample was dried in a vacuum oven above its glass transition temperature, i.e., above 55° C. or 60° C. for PLA materials, under a vacuum of at least 15 inches of mercury with a nitrogen gas purge of at least 30 standard cubic feet per hour (SCFH) for at least 16 hours. When the instrument was warmed up, and the pressure transducer was calibrated, the material sample was loaded incrementally into the column, packing resin into the column with a ramrod each time to ensure a consistent melt during testing. After material sample loading, a 2 minute melt time preceded each test to allow the material sample to completely melt at the test temperature. The capillary rheometer took data points automatically and determined the apparent viscosity (in Pascal second) at 7 apparent shear rates (1/second): 50, 100, 200, 500, 1000, 2000, and 5000.

When examining the resultant curve, it is important that the curve be relatively smooth, if there are significant deviations from a general curve from one point to another, possibly because of air in the column, the test run should be repeated to confirm the results.

The resultant rheology curve of apparent shear rate vs. apparent viscosity produced gave an indication of how the material sample will run at that temperature in an extrusion process. The apparent viscosity values at a shear rate of at least 1000 1/second were of specific interest because these were the typical conditions found in commercial fiber spinning extruders.

Weight/Number Average Molecular Weights

A gel permeation chromatography (GPC) method was used to determine the molecular weight distribution of samples of poly(lactic acid) having a weight average molecular weight (Mw) between 800 to 400,000.

The GPC was setup with two PLgel Mixed K linear 5 micron, 7.5×300 millimeter analytical columns in series. The column and detector temperatures were 30° C. The mobile phase was HPLX grade tetrahydrofuran (THF). The pump rate was 0.8 milliliters per minute with an injection volume of 25 micro liters. Total run time was 30 minutes.

It is important to note that new analytical columns must be installed every 4 months, a new guard column every month, and a new in-line filter every month.

Standards of polystyrene polymers, obtained from Aldrich Chemical Co., should be mixed into solvent of dichloromethane (DCM):THF (10:90), both HPLC. grade, to obtain 1 mg/ml concentrations. Multiple polystyrene standards can be combined in one standard solution provided that their peaks do not overlap when chromatographed. A range of standards of about 687 to 400,000 should be prepared. Examples of standard mixtures with Aldrich polystyrenes of varying molecular weights(in weight average—molecular weight—"M") include: Standard 1 (401,340; 32,660; 2,727), Standard 2 (45,730; 4,075), Standard 3 (95,800; 12,860) and Standard 4 (184,200; 24,150; 687).

Next, prepare the stock check standard. Dissolve 10 g of a 200,000 molecular weight PLA standard, Catalog#19245 obtained from Polysciences Inc., to 100 ml of HPLC. grade DCM to a glass jar with Teflon lined lid using an orbital shaker (at least 30 minutes). Pour out the mixture onto a clean, dry glass plate, first allow the solvent to evaporate, then place in a 35° C. preheated vacuum oven and dry at least 14 hours under a vacuum of 25 mm of Hg. Next remove the PLA from the oven, and cut the film into small strips. Immediately grind the samples using a grinding mill (w/10 mesh screen) taking care not to add too much sample and causing the grinder to freeze up. Store a few grams of the ground sample in a dry glass jar in a dessicator, while the remainder of the sample can be stored in the freezer in a similar type jar.

It is important to prepare a new check standard prior to the beginning of each new sequence, and because the molecular weight is greatly affected by sample concentration, great care should be taken in its weighing and preparation. To prepare the check standard, weigh out 0.0800±0.0025 g of 200,000 Mw PLA reference standard into a clean dry scintillation vial. Then using a volumetric pipet or dedicated repipet, add 2 ml of DCM to the vial and screw the cap on tightly. Allow the sample to dissolve completely. Swirl the sample on an orbital shaker, such as a Thermolyne Roto Mix (type 51300) or similar mixer, if necessary. To evaluate whether dissolved, hold the vial up to the light at a 45° angle. Turn it slowly, and watch the liquid as it flows down the glass. If the bottom of the vial does not appear smooth, the sample is not completely dissolved. It may take the sample several hours to dissolve. When dissolved, add 18 ml of THF using a volumetric pipet or dedicated repipet, cap the vial tightly, and mix.

Sample preparations begin by weighing 0.0800 g±0.0025 g of the sample into a clean, dry scintillation vial. Great care also should be taken in its weighing and preparation. Add 2 ml of DCM to the vial with a volumetric pipet or dedicated repipet, and screw the cap on tightly. Allow the sample to dissolve completely using the same technique described in the check standard preparation above. Then add 18 ml of THF using a volumetric pipet or dedicated repipet, cap the vial tightly, and mix.

Begin the evaluation by making a test injection of a standard preparation to test the system equilibration. When equilibration is confirmed, inject the standard preparations. After those are run, inject the check standard preparation and then the sample preparations. Inject the check standard preparation after every 7 sample injections and at the end of testing. Be sure not to take any more than two injections from any one vial, and those two injections must be made within 4.5 hours of each other.

Four quality control parameters assess the results. First, the correlation coefficient of the fourth order regression calculated for each standard should be not less than 0.950 and not more than 1.050. Second, the relative standard deviation (RSD) of all the Mw's of the check standard preparations should not be more than 5.0 percent. Third, the average of the Mw's of the check standard preparation injections should be within 10 percent of the Mw on the first check standard preparation injection. Lastly, record the lactide response for the 200 microgram per milliliter (pg/mL) standard injection on a SQC data chart.

Using the chart's control lines, the response must be within the defined SQC parameters.

Calculate the Molecular statistics based on the calibration curve generated from the Polystyrene standard preparations and Mark Houwink constants for PLA and Polystyrene in THF at 30° C.

Those are Polystyrene (K=14.1*$10^5$, alpha=0.700) and PLA (K=54.9*$10^5$, alpha=0.639).

Heat Shrinkage of Fibers

The required equipment for the determination of heat shrinkage includes a convection oven (Thelco model 160DM laboratory oven), 0.59 gms (±0.069 gms) sinker weights, ½ inch binder clips, masking tape, graph paper with at least ¼ inch squares, foam posterboard (11 by 14 inches) or equivalent substrate to attach the graph paper and samples. The convection oven should be capable of a temperature of 100° C.

Fiber samples are melt spun at their respective spinning conditions, a 30 filament bundle is preferred, and mechanically drawn to obtain fibers with a jetstretch of 224 or higher. Only fibers of the same jetstretch can be compared to one another in regard to their heat shrinkage. The jetstretch of a fiber is the ratio of the speed of the drawdown roll divided by the linear extrusion rate (distance/time) of the melted polymer exiting the spinneret. The spun fiber is collected onto a bobbin using a winder. The collected fiber bundle is separated into 30 filaments, if a 30 filament bundle has not already been obtained, and cut into 9 inch lengths.

The graph paper is taped onto the posterboard where one edge of the graph paper is matched with the edge of the posterboard. One end of the fiber bundle is taped, no more than the end 1 inch. The taped end is clipped to the posterboard at the edge where the graph paper is matched up such that the edge of the clip rests over one of the horizontal lines on the graph paper while holding the fiber bundle in place (the taped end should be barely visible as it is secured under the clip). The other end of the bundle is pulled taut and lined up parallel to the vertical lines on the graph paper. Next, at 7 inches down from the point where the clip is binding the fiber, pinch the 0.59 gms sinker around the fiber bundle. Repeat the attachment process for each replicate. Three replicates can be attached at one time. Marks can be made on the graph paper to indicate the initial positions of the sinkers. The samples are placed into the 100° C. oven such that they hang vertically and do not touch the posterboard. At time intervals of 5, 10, and 15 minutes, quickly mark the new location of the sinkers on the graph paper and return samples to the oven.

After the testing is complete, remove the posterboard and measure the distances between the origin (where the clip held the fibers) and the marks at 5, 10, and 15 minutes with a ruler graduated to 1/16 inch (about 0.16 cm). Three replicates per sample are recommended. Calculate averages, standard deviations, and percent shrinkage. The percent shrinkage is calculated as (initial length of the fiber minus the final measured length of the fiber) divided by the initial length of the fiber and multiplied by 100. The Heat Shrinkage values reported herein use the values obtained at 15 minutes.

Determination of Crystal Size

Measurement of the crystal sizes within a fiber sample was determined by x-ray diffraction using an x-ray machine, available from Philips Inc. of Mahwah, N.J., under the designation XRG-3000 x-ray machine, outfitted with a copper tube. Photographs were obtained, and a plot was done using a wide angle goniometer. To determine effective crystal size of a fiber sample, a reflection pattern was obtained in the equatorial direction relative to the fiber, scanning through the (hkl) layer line. The (100) plane at about 16.4° 2Q was selected so as to be consistent with all dimension calculations. Using the Scherrer equation, a mean dimension for the crystallites perpendicular to the (100) plane was then calculated.

Biodegradability Testing

Biodegradability testing of samples was carried out by Organic Waste Systems of Gent, Belgium, using a modified ASTM 5338.92, or equivalent ISO CD 14855, testing procedure. The modification from the ASTM 5338.92 method is that the test chambers are maintained at a constant temperature of 58° C. throughout the testing rather than using an incremental temperature profile.

EXAMPLE I

A poly(lactic acid) polymer (PLA) was obtained from Chronopol Inc., Golden, Colo. The poly(lactic acid) polymer had an L:D ratio of 100 to 0, a melting temperature of about 175° C., a weight average molecular weight of about 211,000, a number average molecular weight of about 127,000, a polydispersity index of about 1.66, and a residual lactic acid monomer value of about 5.5 weight percent.

The poly(lactic acid) polymer was mixed with various amounts of adipic acid. The blend of the poly(lactic acid) polymer with the adipic acid involved dry mixing the components followed by melt mixing them together to provide vigorous mixing of the components, which was achieved in a counter-rotating twin screw extruder. Mixing was conducted on either a BRABENDER™ twin screw compounder or a HAAKE™ twin screw extruder with mixing screws.

Conversion of the prepared mixtures into fibers was conducted on a fiber spinning line. The spinning line consists of a ¾ inch diameter single screw extruder with a 24:1 L:D (length:diameter) ratio screw and 3 heating zones which feeds into a 0.62 inch diameter Koch® static mixer unit and then into the spinning head (4th and 5th heating zones) through a spinneret of 15 to 30 holes, where each hole has a diameter of about 500 micrometers. The temperatures of each heating zone were indicated sequentially under the temperature profile section. The fibers were air quenched at 13° C. to 22° C. and drawn down by a mechanical draw roll to either a winder unit or a fiber drawing unit (as in the Lurgi spunbond process). The process conditions for several of the prepared fibers are shown in Table 1.

TABLE 1

| Polymer Blend | Temperature Profile | Comments |
|---|---|---|
| PLA/Adipic acid (100:0) | 160/180/190/190/190 | Needed to drop extruder rate to lower extruder torque and pressure. |
| PLA/Adipic acid (85:15) | 145/155/160/160/160 | Lowered temps used to maintain spinning pressures. |
| PLA/Adipic acid (75:25) | 150/170/165/160/160 | Lowered temps used to maintain spinning pressures. |

The prepared fibers then were evaluated for heat shrinkage, is Tg, and mean crystal size. The results of these evaluations are shown in Table 2. The actual percentage of the poly(lactic acid) polymer/adipic acid ratios were determined by using nuclear magnetic resonance as the ratio between CH and $CH_2$ peaks.

TABLE 2

| Feed Percentage of Adipic | Actual Percentage of Adipic in spun fiber | Tg (° C.) | Mean Crystal Size L(hkl) (in Angstroms) | Percent Heat Shrinkage |
|---|---|---|---|---|
| 0% | 0.0% | 63.4 | 120 | 16.6% |
| 5% | 5.0% | 53.9 | — | — |
| 10% | 9.2% | 41.6 | 100 | 8.9% |
| 15% | — | 45.0 | — | — |
| 25% | 27.1% | 36.9 | 60 | 0% |

EXAMPLE II

A poly(lactic acid) polymer was obtained from Chronopol Inc., Golden, Colo. The poly(lactic acid) polymer had an L:D ratio of 100 to 0, a melting temperature of about 175° C., a weight average molecular weighs of about 181,000, a number average 13 molecular weight of about 115,000, a polydispersity index of about 1.57, and a residual lactic acid monomer value of about 2.3 weight percent.

The poly(lactic acid) polymer was mixed with various amounts of adipic acid. The blend of the poly(lactic acid) polymer with the adipic acid involved dry mixing the components followed by melt mixing them together to provide vigorous mixing of the components, which was achieved in a counter-rotating twin screw extruder. Mixing was conducted on either a BRABENDER™ twin screw compounder or a HAAKE™ twin screw extruder with mixing screws. Conversion of the prepared mixtures into fibers was conducted on a fiber spinning line. The spinning line consisted of a ¾ inch diameter extruder with a 24:1 L:D (length:diameter) ratio screw and 3 heating zones which feed into a 0.62 inch diameter Koch® static mixer unit and then into the spinning head (4th and 5th heating zones) through a spinneret of 15 to 30 holes, where each hole has a diameter of about 500 micrometers. The temperatures of each heating zone were indicated sequentially under the temperature profile section. The fibers were air quenched at 13° C. to 22° C. and drawn down by a mechanical draw roll to either a winder unit or a fiber drawing unit (as in the Lurgi spunbond process). The process conditions for several of the prepared fibers are shown in Table 3.

TABLE 3

| Polymer Blend | Temperature Profile | Comments |
|---|---|---|
| PLA/Adipic acid (100:0) | 180/207/195/195/195 | Needed to drop extruder rate to lower extruder torque and pressure. |
| PLA/Adipic acid (95:5) | 160/185/175/175/175 | Lowered temps used to maintain spinning pressures. |
| PLA/Adipic acid (90:10) | 160/185/175/175/175 | Lowered temps used to maintain spinning pressures. |
| PLA/Adipic acid (85:15) | 150/175/170/170/170 | Lowered temps used to maintain spinning pressures. |
| PLA/Adipic acid (80:20) | 150/175/170/170/170 | Lowered temps used to maintain spinning pressures. |
| PLA/Adipic acid (75:25) | 150/170/168/168/168 | Lowered temps used to maintain spinning pressures. |
| PLA/Adipic acid (70:30) | 150/170/165/165/165 | Lowered temps used to maintain spinning pressures. |

The prepared fibers then were evaluated for heat shrinkage, Tg, and biodegradability. The results of these evaluations are shown in Table 4. The actual percentage of the poly(lactic acid) polymer/adipic acid ratios were determined by using nuclear magnetic resonance as the ratio between CH and $CH_2$ peaks.

TABLE 4

| Feed Percentage of Adipic | Actual Percentage of Adipic in spun fiber | Tg (° C.) | Biodegradation after 45 days | Percent Heat Shrinkage |
|---|---|---|---|---|
| 0% | 0.0% | 56.5 | 76.1% | 34% |
| 5% | 5.2% | — | — | 40% |
| 10% | 9.2% | 49.5 | 92.5% | 10% |
| 15% | 18.3% | 50.9 | — | 7% |
| 20% | 12.1% | — | — | 14% |
| 25% | 19.7% | 49.4 | 100% | 12% |
| 30% | 21.6% | 49.4 | — | 0% |

The process of the present invention is capable of modifications and variations without departing from the scope thereof. Accordingly, the detailed description and examples set forth above are meant to be illustrative only and are not intended to limit the scope of the invention as set forth in the appended claims.

What is claimed is:

1. A process for forming a synthetic fiber, comprising:
   a. providing a first component of an aliphatic polyester polymer;
   b. providing a second component of a multicarboxylic acid;
   c. mixing said first component aliphatic polyester polymer and said second component multicarboxylic acid to form an unreacted specified thermoplastic composition;
   d. melt blending said unreacted specified thermoplastic composition in an extruder or mixer;
   e. lubricating said extruder by said second component multicarboxylic acid;
   f. providing a nucleating agent provided by said second component multicarboxylic acid; and
   g. crystallizing said specified thermoplastic composition in the presence of said second component multicarboxylic acid nucleating agent to form a mean crystal size less than about 120 Angstroms.

2. A process for forming a synthetic fiber as set forth in claim 1, further comprising:

h. forming a fiber composed of said specified thermoplastic composition having a mean crystal size less than about 120 Angstroms.

3. A process for forming a synthetic fiber as set forth in claim 2, further comprising:

i. forming a nonwoven web from said fiber composed of said specified thermoplastic composition having a mean crystal size less than about 120 Angstroms.

4. A process for forming a synthetic fiber as set forth in claim 2, wherein said forming a fiber comprises forming a fiber having a glass transition temperature (Tg) of at least 3° C. less than said first component aliphatic polyester polymer.

5. A process for forming a synthetic fiber as set forth in claim 2, wherein said lubricating said extruder by said second component multicarboxylic acid comprises replacing secondary valence bonds holding together said aliphatic polyester polymer with multicarboxylic acid-to-aliphatic polyester polymer valence bonds.

6. A process for forming a synthetic fiber as set forth in claim 2, wherein said first component comprises polylactic acid.

7. A process for forming a synthetic fiber as set forth in claim 2, wherein said first component comprises polylactic acid and said second component comprises adipic acid.

8. A process for forming a synthetic fiber as set forth in claim 2, wherein said forming a fiber comprises melt spinning said specified thermoplastic composition having a mean crystal size less than about 120 Angstroms.

9. A process for forming a synthetic fiber as set forth in claim 2, wherein said forming a fiber comprises pelletizing said specified thermoplastic composition to form pellets of said specified thermoplastic composition having a mean crystal size less than about 120 Angstroms.

10. A process for forming a synthetic fiber as set forth in claim 2, wherein said forming a fiber comprises pelletizing said specified thermoplastic composition to form pellets of said specified thermoplastic composition and subsequent melting and melt spinning of said pellets.

11. A process for forming a synthetic fiber as set forth in claim 2, further comprising modifying the stereochemistry of said first component to control melting temperature, melt rheology, and crystallinity of said first component.

12. A process for forming a synthetic fiber as set forth in claim 2, further comprising modifying the stereochemistry of said first component to control melting temperature, melt rheology, and crystallinity of said first component and form a multicomponent fiber having preferred melt strength, mechanical properties, softness, and processability properties to make attenuated, heat set, and crimped fibers.

13. A process for forming a synthetic fiber as set forth in claim 2, wherein said forming a fiber comprises forming a fiber having thermal-dimensional stability.

14. A process for forming a synthetic fiber as set forth in claim 2, wherein said forming a fiber comprises forming a fiber having biodegradability.

15. A process for forming a synthetic fiber as set forth in claim 2, wherein said aliphatic polyester polymer has a weight average molecular weight between about 10,000 to about 2,000,000, wherein the aliphatic polyester polymer is present in the specified thermoplastic composition in a weight amount that is between about 60 weight percent to about 80 weight percent; and said multicarboxylic acid has a total of carbon atoms less than about 30, wherein the multicarboxylic acid is present in the specified thermoplastic composition in a weight amount that is between about 20 weight percent to about 40 weight percent, wherein all weight percents are based on the total weight amount of the aliphatic polyester polymer and the multicarboxylic acid present in the specified thermoplastic composition.

16. A process for forming a synthetic fiber as set forth in claim 2, wherein said aliphatic polyester polymer is present in the specified thermoplastic composition in a weight amount that is between about 70 weight percent to about 75 weight percent.

17. A process for forming a synthetic fiber as set forth in claim 2, wherein said multicarboxylic acid is present in the specified thermoplastic composition in a weight amount between about 25 weight percent to about 30 weight percent.

18. A process for forming a synthetic fiber as set forth in claim 2, wherein said aliphatic polyester polymer has a weight average molecular weight between about 10,000 to about 2,000,000, wherein the aliphatic polyester polymer is present in the specified thermoplastic composition in a weight amount that is between about 50 weight percent to about 95 weight percent and said multicarboxylic acid has a total of carbon atoms less than 30, wherein the multicarboxylic acid is present in the specified thermoplastic composition in a weight amount between about 5 weight percent to about 50 weight percent, wherein all weight percents are based on the total weight amount of the aliphatic polyester polymer and the multicarboxylic acid present in the specified thermoplastic composition said wherein the fiber exhibits a Heat Shrinkage value less than about 15 percent.

19. A process for forming a synthetic fiber as set forth in claim 2, wherein said forming a fiber comprises forming a fiber having a glass transition temperature (Tg) of at least 5° C. less than said first component aliphatic polyester polymer.

20. A process for forming a synthetic fiber as set forth in claim 2, wherein said forming a fiber comprises forming a fiber having a glass transition temperature (Tg) of at least about 10° C. less than said first component aliphatic polyester polymer.

21. A process for forming a synthetic fiber as set forth in claim 2, wherein said forming a fiber comprises forming a fiber having a glass transition temperature (Tg) of at least about 20° C. less than said first component aliphatic polyester polymer.

22. A process for forming a synthetic fiber, comprising:

a. providing a first component of an aliphatic polyester polymer;

b. providing a second component of a multicarboxylic acid;

c. dry mixing said first component aliphatic polyester polymer and said second component multicarboxylic acid to form an unreacted specified thermoplastic composition;

d. melt blending said unreacted specified thermoplastic composition in an extruder or mixer;

e. lubricating said extruder by said second component multicarboxylic acid;

f. providing a nucleating agent provided by said second component multicarboxylic acid;

g. crystallizing said specified thermoplastic composition in the presence of said second component multicarboxylic acid nucleating agent to form a mean crystal size less than about 120 Angstroms;

h. forming a fiber composed of said specified thermoplastic composition having a mean crystal size less than about 120 Angstroms; and i. forming a nonwoven web absorbent article from said fiber composed of said specified thermoplastic composition having a mean crystal size less than about 120 Angstroms.

23. A process for forming a synthetic fiber as set forth in claim 22, wherein said forming a fiber comprises forming a fiber having a glass transition temperature (Tg) of at least about 10° C. less than said first component aliphatic polyester polymer.

24. A nonwoven web absorbent article formed from a fiber composed of a specified thermoplastic composition having a mean crystal size less than about 120 Angstroms, wherein said fiber is formed by:

a. providing a first component of an aliphatic polyester polymer;
   b. providing a second component of a multicarboxylic acid;
   c. dry mixing said first component aliphatic polyester polymer and said second component multicarboxylic acid to form an unreacted specified thermoplastic composition;
   d. melt blending said unreacted specified thermoplastic composition in an extruder or mixer;
   e. lubricating said extruder by said second component multicarboxylic acid;
   f. providing a nucleating agent provided by said second component multicarboxylic acid;
   g. crystallizing said specified thermoplastic composition in the presence of said second component multicarboxylic acid nucleating agent to form a mean crystal size less than about 120 Angstroms;
   h. forming a fiber composed of said specified thermoplastic composition having a mean crystal size less than about 120 Angstroms; and
   i. forming a nonwoven web absorbent article from said fiber composed of said specified thermoplastic composition having a mean crystal size less than about 120 Angstroms.

* * * * *